United States Patent [19]

Rigby

[11] 4,445,510

[45] May 1, 1984

[54] AUTOMATIC INJECTOR FOR HYPODERMIC SYRINGES OR THE LIKE AND LANCET HOLDER FOR USE IN CONJUNCTION WITH AN AUTOMATIC INJECTOR

[76] Inventor: Ronald F. Rigby, P.O. Box 341 (R.D. 6), Latrobe, Pa. 15650

[21] Appl. No.: 417,607

[22] Filed: Sep. 13, 1982

[51] Int. Cl.³ ............................................. A61B 17/34
[52] U.S. Cl. ............................................... 128/329 R
[58] Field of Search .................... 128/329 R, 314, 315; 604/157, 156, 93

[56] References Cited

U.S. PATENT DOCUMENTS

| | | | |
|---|---|---|---|
| 2,442,416 | 6/1948 | Kulicke, Jr. et al. | 128/329 R |
| 3,030,959 | 4/1962 | Grunert | 128/314 X |
| 3,208,452 | 9/1965 | Stern | 128/329 R |
| 3,612,051 | 10/1971 | Arce | 128/329 R |
| 4,203,446 | 5/1980 | Hofert et al. | 128/329 R |

Primary Examiner—John D. Yasko
Attorney, Agent, or Firm—Lerner, David, Littenberg, Krumholz & Mentlik

[57] ABSTRACT

An apparatus for propelling an elongated device including a sharp object such as a hypodermic syringe and needle or the like into biological tissue, the apparatus including an inner sleeve for carrying the hypodermic syringe or the like and an outer sleeve in which the inner sleeve reciprocates, biasing means being provided for biasing the inner sleeve relative to the outer sleeve. The locking sleeve receives therein the outer sleeve and through at least one recess and ball bearing arrangement, the inner sleeve can be locked relative to the outer sleeve. When the locking sleeve is forced against biological tissue, the ball bearing or bearings release the locked relationship between the inner and outer sleeves and propel the needle of the hypodermic syringe or the like into the biological tissue. An improvement in assembly is provided by the present invention such that the ball bearings can be placed in position without the boring of a ball bearing loading aperture in the locking sleeve. Additionally, a lancet holder is provided which simulates the shape of a syringe. The lancet holder carries a lancet for insertion into the aforedescribed apparatus for utilization in taking of blood samples or the like.

14 Claims, 12 Drawing Figures

AUTOMATIC INJECTOR FOR HYPODERMIC SYRINGES OR THE LIKE AND LANCET HOLDER FOR USE IN CONJUNCTION WITH AN AUTOMATIC INJECTOR

BACKGROUND AND/OR ENVIRONMENT OF THE INVENTION

1. Field of the Invention

The present invention relates to apparatuses for propelling elongated devices including a sharp object, such a hypodermic syringe and needle or the like, into biological tissue, and more particularly to means of facilitating the assembly of such an apparatus and means for adapting such an apparatus for use in conjunction with a conventional lancet for taking of blood samples or the like.

2. Description of the Contemporary and/or Prior Art

The psychological as well as physiological trauma associated with the injection of therapeutic substances into living bodies by way of the needle of a hypodermic syringe or the like and the puncturing of biological tissue to take blood samples is well known to anyone experiencing or delivering such procedures. Furthermore, for patients which must self-inject themselves, such as diabetics who undergo continuous insulin therapy, and have only a limited number of sites into which insulin can be injected because of the limits of the patient's reach during self-injection, the shortcomings of an unadorned conventional hypodermic syringe are also well known. For example, it is quite difficult for a diabetic to self-inject into the normal injection site on the upper portion of the arm because of the inconvenience of reach. Therefore, it has long been desirable to provide an apparatus which will aid a diabetic in self-injection.

It is also desirable, especially in injecting children, to camouflage the hypodermic syringe so that the presence of the needle thereof is not overwhelming. Additionally, pain can be minimized if insertion of a hypodermic needle is quick and even, a set of circumstances which are not always obtainable under direct human control. Furthermore, since it is frequently necessary for family members who are unskilled in injection techniques to inject patients, it is quite desirable to have an automatic injector which holds a conventional hypodermic syringe and which, upon release, quickly causes the needle of the hypodermic syringe to be propelled into biological tissue so that therapeutic fluids can be injected.

Prior attempts to produce such automatic devices are known but unfortunately these devices have failed, not because of their performance when they worked, but because of design flaws which caused malfunctions and jamming. Especially in a medical apparatus, reliability and repeatability of function is of primary importance and therefore such previously known devices have not enjoyed widespread use.

Illustrative of prior art devices is that disclosed in U.S. Pat. No. 2,664,086 issued to G. O. Transue on Dec. 29, 1953. Another similar apparatus is discussed in the Journal of the American Medical Association, Apr. 14, 1956, page 1308, in an article entitled "A New Injector Designed to Minimize Pain and Apprehension of Parenteral Therapy" by Figge and Gelhause.

A further prior art apparatus is illustrated in FIGS. 10, 11, and 12 of the present application. All of these apparatuses basically include a member for holding the syringe and means for shifting the syringe out of a housing upon release of the engagement of the syringe holding element and the housing. Engagement and temporary locking of the elements of these apparatuses has been accomplished by use of ball bearings which engage recesses and apertures in the elements of these apparatuses. In some instances the ball bearings have been placed in position by deformation of the elements and forcing of the ball bearings into position, aided by sloppy tolerances of the elements. In other instances, such as the apparatus illustrated in FIGS. 10-12 of the present application, insertion of the ball bearings have been accomplished through the boring of a ball bearing delivery aperture in a selected element. The ball bearings are positioned by placement through this aperture and the plugging of the aperture after insertion of the ball bearings. This has not proven to be satisfactory since the plugged aperture presents a weak spot in the assembly and, if the plug either extends too far or not enough in the aperture, it can be cause for jamming of the apparatus. While such jamming can be rectified, it is not a very pleasant situation if it takes place during the process of injection by the apparatus.

The present invention overcomes the shortcomings associated with the prior art by providing a configuration of elements which permits assembly without the deformation of any of the elements of the invention or the boring of a ball bearing delivery aperture. Therefore, the present invention avoids the jamming problems associated with the prior art.

Another procedure which requires the piercing of a patient's skin by a sharp object is in the use of a lancet for piercing a fingertip or other site to obtain a drop of blood for blood testing. While such a procedure may only be an occasional nuisance for most patients, some patients, such as certain diabetics, must test their blood numerous times during the day for certain types of therapy. For instance, the diabetics undergoing this particular type of therapy may have to pierce their fingertips or other sites as many as four times a day. The trauma associated with this process is not insignificant and the importance of making a quick and clean puncture is magnified. Apparatuses are known in the prior art for forcing the point of a lancet into a fingertip or the like by mechanical means. For instance, a device is marketed by Ulster Scientific under the trade name Autolet. The Autolet apparatus engages a lancet in a spring loaded member which is released by pushing of a trigger, this release propelling the sharp point of the lancet into a selected tissue site.

Heretofore, a patient needing to take blood samples and also needing to take injections required two separate devices if automated insertion was to be accomplished. In contrast, the present invention provides a lancet holder which is simulative in shape of a hypodermic syringe so that the holder can be used in an automatic injector, such as the type taught by the present invention, for automatic insertion of a lancet point into a selected tissue site.

SUMMARY OF THE INVENTION

Therefore, a primary object of the present invention is to provide an apparatus for propelling the needle of a hypodermic syringe or the like into biological tissue.

A further object of the present invention is to provide an apparatus for propelling a hypodermic syringe needle into biological tissue quickly and with uniform pressure.

A still further object of the present invention is to provide an automatic apparatus for propelling the needle of a hypodermic syringe or the like into biological tissue which is not subject to jamming.

Still another object of the present invention is to provide an apparatus for automatically propelling the needle of a hypodermic syringe into selected biological tissue wherein the needle of the syringe is hidden until after injection.

Still another further object of the present invention is to provide an apparatus for holding a lancet so that it can be used in conjunction with an automatic injection apparatus designed for use with a hypodermic syringe or the like.

Another still further object of the present invention is to provide an apparatus for propelling the needle of a hypodermic syringe or the like into biological tissue which is relatively quick and easy to assemble during manufacture and which is capable of an extended trouble free lifetime.

An additional object of the present invention is to provide an apparatus for propelling a sharp object such as a hypodermic syringe and needle or the like into biological tissue which is simple in design, relatively inexpensive to manufacture, rugged in construction, easy to use, and efficient in operation. It is also similarly an object of the present invention to provide a holder for a lancet for use in conjunction with an automatic injector apparatus which embodies these same characteristics.

These objects, as well as further objects and advantages of the present invention, will be readily apparent after reading the ensuing description of a nonlimiting illustrative embodiment and viewing the accompanying drawing.

An apparatus for propelling an elongated device including a sharp object, such as a hypodermic syringe and needle, or the like into biological tissue, according to the principles of the present invention, comprises: an inner sleeve forming an open-ended longitudinal chamber therein for receiving an elongated device including a sharp object, the inner sleeve for removably retaining therein the elongated device, the inner sleeve having first and second spaced apart recesses disposed in the outer surface thereof, the first recess being of a greater depth than the second recess; an outer sleeve forming an open-ended longitudinal chamber therein for receiving and for permitting the reciprocation therein of the inner sleeve, the outer sleeve having at least one aperture disposed therethrough; biasing means for biasing the inner sleeve relative to the outer sleeve; ball bearing means dimensioned to reside within the at least one aperture and to selectively reside within the second recess when aligned with the aperture; and locking sleeve means forming an open-ended longitudinal chamber therein for reciprocally receiving therein a portion of the outer sleeve adjacent to the at least one aperture disposed therein, the locking sleeve providing a raised surface on the inner wall of the longitudinal chamber thereof for forcing the ball bearing means into the second recess so as to lock the position of the inner sleeve relative to the outer sleeve, longitudinal force on the locking sleeve in a predetermined direction causing the ball bearing means to disengage the raised surface and the inner sleeve to shift position relative to the outer sleeve as a result of the action of the biasing means thereon, the first recess being provided to accept the ball bearing means during assembly of the apparatus, the first recess being of sufficient depth to permit the passage of the locking sleeve means over the ball bearing means during assembly.

A lancet holder for use in conjunction with an apparatus for propelling the needle of a hypodermic syringe into biological tissue, according to the principles of the present invention, comprises: an elongated body portion having first and second ends; a head portion disposed at the first end of the elongated body portion, the head portion and the body portion substantially simulating the shape of a hypodermic syringe; and retaining means for retaining a portion of a lancet disposed adjacent to the second end of the elongated body portion.

BRIEF DESCRIPTION OF THE DRAWINGS

In order that the present invention may be more fully understood it will now be described, by way of example, with reference to the accompanying drawings in which.

DESCRIPTION OF THE PREFERRED EMBODIMENT

Figure 1:
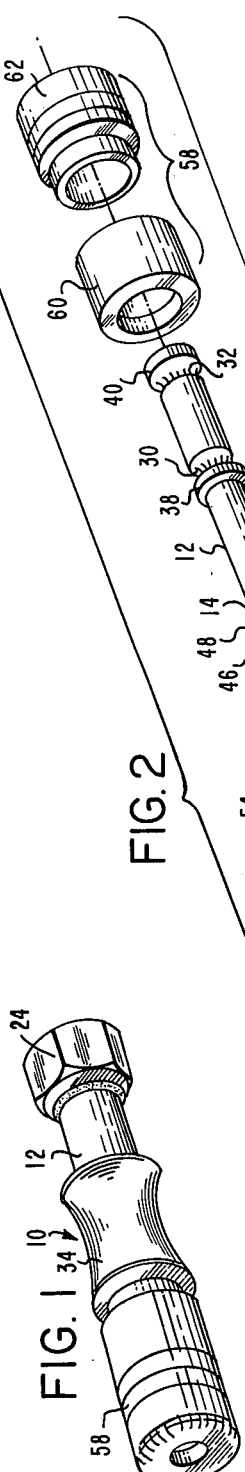
FIG. 1 is a perspective view of the preferred embodiment of the present invention.
Figure 2:
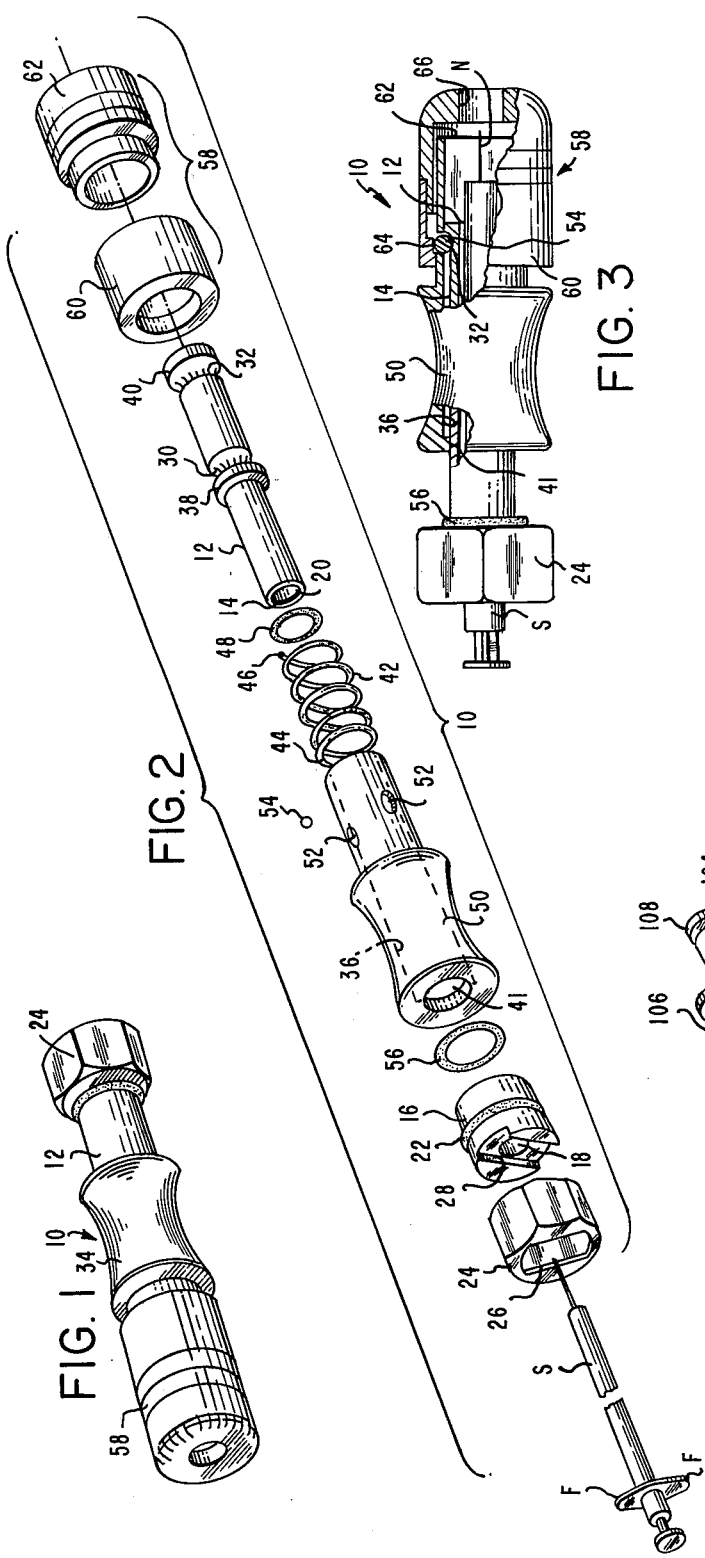
FIG. 2 is an exploded view of the preferred embodiment of the present invention.

Referring now to the figures, and more particularly to FIGS. 1 and 2 thereof, there is illustrated therein an automatic injector apparatus 10. The automatic injector apparatus 10 is used to propel a sharpened portion of an elongated device into biological tissue or the like. For example, a hypodermic syringe and needle can be used in conjunction with the automatic injector apparatus 10 to cause the needle thereof to be inserted into the skin of a patient so that therapeutic fluid can be delivered by the syringe.

The automatic injector apparatus 10, which accepts a syringe S, is assembled from a plurality of components shown in FIG. 2. The hypodermic syringe S is received in an inner sleeve 12 as further illustrated in FIGS. 3 and 4, such that the barrel of the syringe S is disposed within a longitudinal chamber 14 formed by the inner sleeve 12. When the apparatus 10 is assembled, as hereinafter discussed in conjunction with FIGS. 3 through 8, a cap 16 forming a longitudinal chamber 18 therein is fixedly secured to an end 20 of the inner sleeve 12 such that the longitudinal chambers 14 and 18 are coaxial. These components can be press fitted together or otherwise joined.

Disposed about the circumference of the cap 16 is an "O" ring 22 which frictionally engages the inner walls of a hollow hexagonal cap cover 24 such that the cap cover can freely rotate on the "O" ring 22. This is a result of the cap cover having an annular recess, not shown, disposed in the interior walls thereof to capture a portion of the "O" ring 22. The cap cover 24 has disposed therein an elongated substantially rectangular opening 26 dimensioned to permit passage therethrough of the flanges F of the syringe S when positioned within the apparatus 10. The flanges then come to rest in a notch 28 disposed in an end of the cap 16. When the cap cover 24 is then rotated relative to the cap 16, the flange F of the syringe S is locked between the cap cover 24 and the cap 16, therefore precluding unwanted removal or disengagement of the syring S from the inner sleeve 12.

The inner sleeve 12 includes a first recess 30 and a second recess 32 which are annular in shape and which are spaced apart along the longitudinal axis of the inner sleeve 12. The annular recesses 30 and 32 are of different depths, the first annular recess 30 being deeper than the second annular recess 32. The first annular recess is provided to facilitate assembly of the apparatus 10 while the second annular recess 32 is provided to permit locking of the apparatus 10 in a cocked position as hereinafter described.

Figure 3:
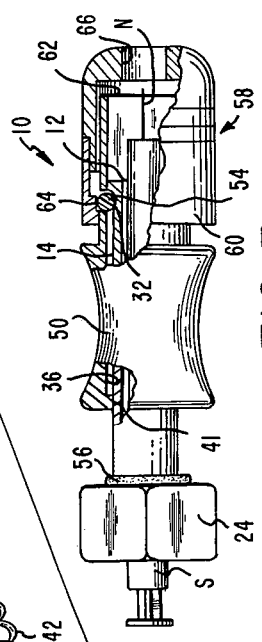
FIG. 3 is a partially broken away side elevation of the present invention showing a hypodermic syringe in position with the present invention being in a cocked position.

The apparatus 10 further includes an outer sleeve 34 which forms a longitudinal chamber 36 therein. The longitudinal chamber 36 is dimensioned to receive and permit the reciprocation therein of the inner sleeve 12. The longitudinal chamber 36 is dimensioned so that it is just slightly larger than the largest diameter of the inner sleeve 12 presented by the ridges 38 and 40 thereof which are disposed, respectively, adjacent to the first and second annular recesses 30 and 32. The longitudinal chamber 36 has a neck 41 at one end thereof which is reduced in diameter, as shown in FIG. 3, to preclude movement of the ridge 38 out of the chamber 36 when it is urged toward the neck 41.

A helical compression spring 42 is provided to bias the inner sleeve 12 relative to the outer sleeve 34. When the apparatus 10 is assembled, the end 44 of the spring 42 rests against a ridge, not illustrated, provided within the longitudinal chamber 36 of the outer sleeve 34 and the end 46 of the helical spring 42 rests against a washer 48 which receives therethrough a portion of the inner sleeve 12. The washer 48 in turn rests against the ridge 38. As a result, when the inner sleeve 12 is inserted in the outer sleeve 34, the spring 42 causes these elements to be urged apart. The portion 50 of the outer sleeve 34 is tapered as illustrated to facilitate grasping by the user.

A plurality of radially disposed apertures 52 are disposed through the walls of the outer sleeve 34 and are dimensioned so that they can receive therein one of a plurality of ball bearings 54. The preferred embodiment of the present invention incorporates at least three apertures 52, each aperture being equidistantly spaced around the circumference of the outer sleeve 34 and for receiving a ball bearing 54 therein.

Figure 4:
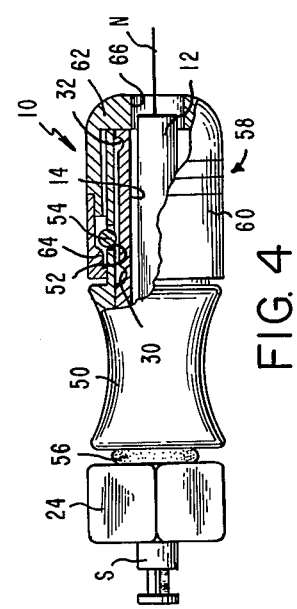
FIG. 4 is a partially broken away side elevation of the present invention showing a hypodermic syringe in position with the present invention being in a released position.

Prior to the fitting of the cap 16 on the inner sleeve 12 an "O" ring 56 is slipped over the outer surface of the inner sleeve 12 to act as a shock absorber when the automatic injector apparatus 10 is released from a cocked position, as further shown in FIG. 4.

The inner sleeve 12 is temporarily locked into a cocked position relative to the outer sleeve 34 by the ball bearings 54 residing simultaneously in the apertures 52 and the recess 32. The ball bearings are forced into this position by a locking sleeve 58 comprising a collar portion 60 and a nose portion 62. The collar portion 60 is fixedly secured to the nose portion 62 when the apparatus 10 is assembled. The collar portion 60 includes an annular interior raised surface 64, further illustrated in FIGS. 3 and 4, which urges the ball bearings 52 into the annular recess 32 when the inner sleeve 12 is shifted longitudinally relative to the outer sleeve 34 such that the apertures 52 are aligned with the recess 32. Although the locking sleeve 58 is illustrated as being constructed from two separate pieces, it is so constructed to facilitate the machining of such elements when constructed of metal and, could be fabricated in one piece, if desired, depending upon the specific type of material and fabrication technique employed.

The operation of the present invention can be best observed with reference to FIGS. 3 and 4. FIG. 3 shows the present invention in a cocked position ready for use and FIG. 4 shows the present invention in a released position wherein the needle N of the hypodermic syringe S protrudes from an opening 64 in the nose portion 62 of the locking sleeve 58. In FIGS. 3 and 4, the syringe S is inserted within the longitudinal chamber 14 of the inner sleeve 12. The syringe S is secured to the inner sleeve 12 by insertion of the flanges F thereof within the notch 28 of the cap 16 and by the rotation of the cap cover 24 to lock the syringe S in position. In the non-cocked or rest position, as shown in FIG. 4, the ball bearings 54 reside within the apertures 52 and ride on the surface of the inner sleeve 12 between the spaced apart annular first and second recesses 30 and 32.

In order to place the apparatus 10 in a cocked position, as illustrated in FIG. 3, the user grasps the cap cover 24 in one hand while holding the tapered portion 50 of the outer sleeve 34 as the automatic injector apparatus 10 is held in a substantially vertical position. By drawing the inner sleeve 12, via the cap cover 24, away from the tapered portion 50 of the outer sleeve 34, the spring 42 is compressed and the needle N of the syringe S is drawn within the locking sleeve 58. Through the effect of gravity on the locking sleeve 58, it is urged away from the tapered portion 50 of the outer sleeve 34 and, as it falls, the annular raised surface 64 causes the ball bearings 54 to be forced inwardly against the inner sleeve 12. Therefore, when the inner sleeve is drawn far enough relative to the outer sleeve 34 so that the second annular recess 32 is aligned with the apertures 52, the ball bearings 54 disposed therein are forced into the second annular recess 32 causing locking of the inner sleeve 12 relative to the outer sleeve 34. The annular raised surface 64 has the leading edge thereof beveled to form a ramp to facilitate movement of the ball bearings 54 onto the annular raised surface 64.

When the apparatus 10 is in the cocked position, slight pressure on the nose portion 62 of the locking sleeve 58 will cause the annular raised surface 64 to leave position over the ball bearings 54 thereby permitting the ball bearings to be forced out of the second annular recess 32 disposed in the inner sleeve 12. When this happens, the inner sleeve 12 is no longer locked into position relative to the outer sleeve 34 and the inner sleeve 12 is urged by the helical spring 42 so that it thrusts the needle N out of the opening 66 in the nose portion 62 of the locking sleeve 58.

When the apparatus 10 is in use, the pressure placed against the nose portion 62 would be occasioned by the user gripping the tapered portion 50 of the outer sleeve 34 and gently pressing the nose portion 62 of the locking sleeve 58 against the site into which the needle N is to be inserted. This gentle pressure causes movement of the annular raised surface 64 within the collar portion 60 of the locking sleeve 58 and causes movement of the ball bearings 54 out of the second annular recess 32 resulting in disengagement of the locking of the inner sleeve 12 and the outer sleeve 34. To cushion the end of travel of the relative movement of the inner sleeve 12 and the outer sleeve 34, the "O" ring 56 is provided as a shock absorber between the end of the tapered surface 50 of the outer sleeve 34 and the bottom surface of the cap 16.

Figure 5:
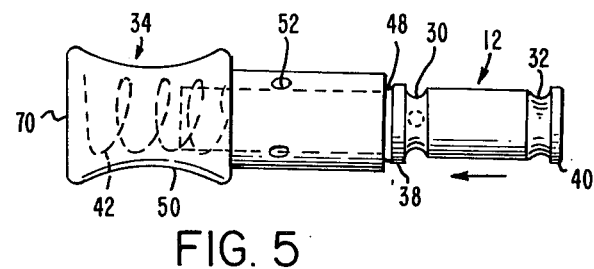
FIGS. 5, 6, 7, and 8 are successive side views of the components of the present invention during assembly, the assembly progressing in steps from FIG. 5 through FIG. 8.
Figure 6:
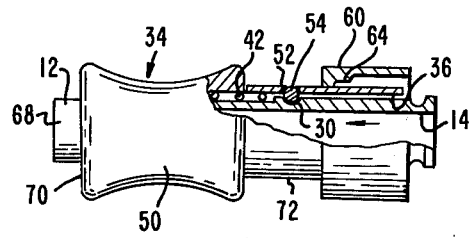
Figure 7:
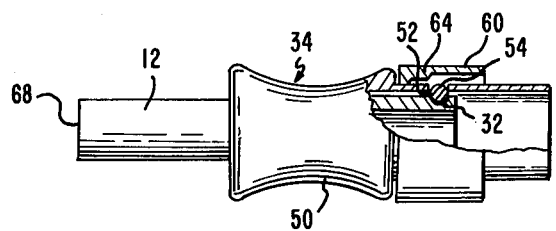
Figure 8:
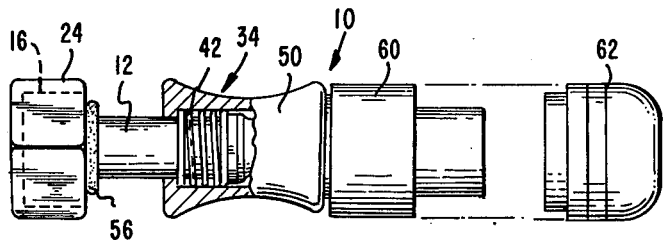

FIGS. 5 through 8 illustrate the manner in which the automatic injector apparatus 10 is assembled. During assembly, the washer 48 and the helical spring 42 are slipped over the inner sleeve 12 as illustrated in FIG. 5. The inner sleeve 12 is then pushed into the longitudinal chamber 36 of the outer sleeve 34 until the end 68 of the inner sleeve 12 extends out of the end 70 of the outer sleeve 34, as illustrated in FIG. 6, thereby aligning the radially disposed apertures 52 with the first annular recess 30. The first annular recess 30 is of a depth sufficient to accept the ball bearings 54 therein so that they fall below the outer surface of the outer sleeve 34 as illustrated in FIG. 6. This permits passage of the collar portion 60 over the portion 72 of the outer sleeve 34, which has the apertures 52 disposed therein, so that the collar portion 60 can reside in the position illustrated in FIG. 7. The cap 16 is then fitted to the portion of the inner sleeve 12 adjacent to the end 68 thereof as illustrated in FIG. 8. The inner sleeve 12 is dimensioned in conjunction with the spacing of the first and second annular recesses 30 and 32 such that once the cap 16 is fixedly secured thereto the ball bearings 54 ride on the surface of the inner sleeve disposed between the first and second annular recesses 30 and 32 but can no longer enter the first recess 30 which is solely used for assembly purposes. When the end of the inner sleeve 12 carrying the cap 16 is drawn back far enough, as hereinbefore described, the ball bearings 54 are forced into the second recess 32 by the annular raised surface 64 disposed in the interior of the collar portion 60 of the locking sleeve 58. As illustrated, the locking sleeve 58 is shown as being constructed in separate sections, the collar portion 60 and the nose portion 62, to facilitate machining of these parts but, the locking sleeve can be made out of a unitary structure if desired.

It therefore should be understood that the first annular recess 30 presents structure for temporarily permitting the ball bearings 54 to recede into the inner sleeve 12 a sufficient distance so that the ball bearings 54 do not protrude out of the apertures 54 thereby permitting the collar portion 60, which has an inner diameter just slightly larger than the outer diameter of the outer sleeve 34, to slide over the apertures 52, having the ball bearings 54 disposed therein. Once the inner sleeve 12 is drawn further back and the cap 16 is affixed thereto, the ball bearings can no longer fall into the first recess 30 and they are securely positioned without necessitating the deformation of any of the parts of the present invention or the provision of a ball bearing loading hole as has been provided in some prior art devices.

Figure 10:
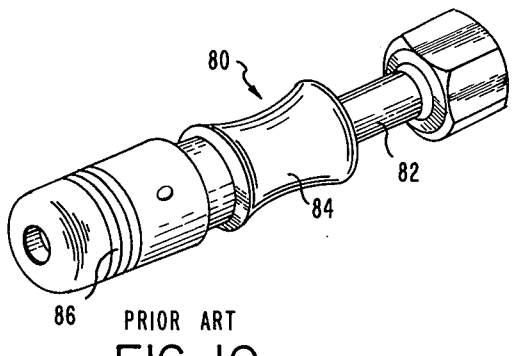
FIG. 10 is a perspective view of a prior art apparatus.
Figure 11:
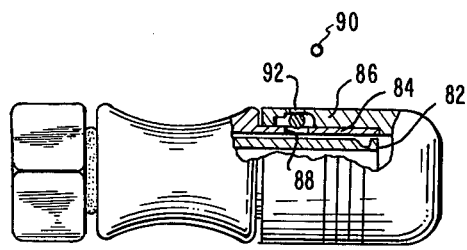
FIG. 11 is a side elevational view, partially broken away, to show the prior art apparatus of FIG. 10 in one stage of assembly.
Figure 12:
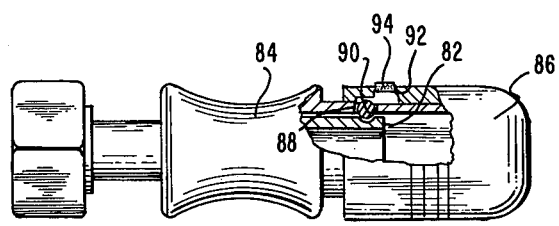
FIG. 12 is a side elevational view of the prior art apparatus of FIGS. 10 and 11 with a portion thereof partially broken away to show the completed assembly.

An apparatus typical of prior art devices which include ball bearing loading apertures is illustrated in FIGS. 10 through 12. The prior art apparatus 80 includes an inner sleeve 82, an outer sleeve 84, and a locking sleeve 86. An aperture 88 is disposed in the outer sleeve 84 and is provided to capture therein a ball bearing 90. This prior art apparatus is assembled by placing the inner sleeve 82 thereof in the outer sleeve 84 thereof and then placing the locking sleeve 86 in position over the outer sleeve 84. As further illustrated in FIGS. 11 and 12, the outer sleeve 84 has a ball bearing loading aperture 92 disposed therein. A ball bearing is dropped into the aperture 88 through the ball bearing loading aperture 92 after alignment of the apertures 88 and 92. After this ball bearing is in position, the locking sleeve must be rotated until the ball bearing loading aperture 92 is aligned with another aperture 88 and this process is continued until all the ball bearings 90 are in position.

After all the ball bearings are in position in the apertures 88, the ball bearing loading aperture 92 is plugged with a plug 94 which preclude the ball bearings 90 from falling out. The plug 94 must be precisely placed because if it is too long it will cause the ball bearings 90 to hang up jamming the apparatus and if it is too short not only can jamming occur but accidental release, a very poor shortcoming, can also possibly occur. In contrast to the previously described prior art apparatus, the present invention totally eliminates the need for a ball bearing loading aperture and a plug, therefore avoiding the shortcomings of the prior art and providing for a faster and easier assembly procedure. The use of a second annular recess in the inner sleeve of an automatic injector is not shown or suggested anywhere in the prior art and heretofore loading of ball bearings was either accomplished, as previously mentioned, by the use of a ball bearing loading aperture or the deformation of the parts of an injector to accommodate the forcing of a ball bearing in position, a condition which dictates sloppy tolerances and therefore a marginally effective apparatus.

Figure 9:
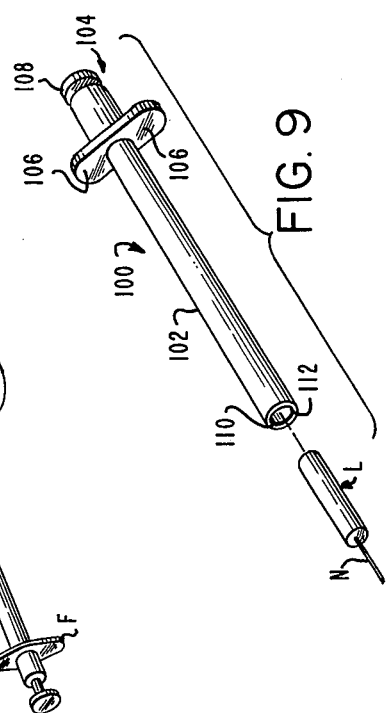
FIG. 9 is a perspective view of the lancet adapter of the present invention and a lancet to be retained therein.

With reference to FIG. 9, there is illustrated therein a lancet holder 100. Lancet holder 100 comprises an elongated body portion 102 and a head portion 104. The head portion 104 includes flanges 106, the head portion 104 and the body portion 102 substantially simulating the shape of a hypodermic syringe. The head portion 104 further includes a recess 108 disposed therein to facilitate the gripping thereof by the user. The end 110 of the elongated body portion 102 has a recess 112 dimensioned for receiving therein the body of a lancet L having a sharpened needle N. The lancet L is of a conventional design and typically comprises a cylindrical plastic body into which is embedded a longitudinal steel rod having a sharpened end forming the needle N. The recess 112 is dimensioned to receive and removably frictionally retain therein the cylindrical body of the lancet L. When the lancet L is so inserted, the lancet holder 110 and lancet L effectively have the same shape as a hypodermic syringe and needle. Therefore, the holder can be loaded into the aforedescribed automatic injector apparatus or any similar apparatus designed for automatic injection of a hypodermic syringe needle. As a result, the lancet L, which is commonly used to make small openings in tissue for blood samples, can be propelled into tissue with the same speed, accuracy, and constant pressure which is provided when such an automatic injector apparatus is employed to inject or propel a needle into biological tissue. Therefore, through use of the lancet holder 100, an apparatus which has previously only been able to be used with hypodermic syringes can now also be used with lancets thereby obviating the need for purchasing a separate injector for use with the lancets. Although one retention means for the lancet is illustrated in the form of a recess 112, it is to be understood that any suitable means for grasping of the lancet by the holder can be employed and clamps or the like or frictional engagement means other than illustrated can be employed, as are well known by those of ordinary skill in the art, within the principles and scope of the invention.

Most of the components of the automatic injector apparatus and the lancet holder have been machined from aluminum in models of the present invention which have been constructed. However, it is recognized that various other materials including plastics can be used to construct the various pieces of the present invention.

Furthermore, it will be understood that various changes in the details, materials, arrangements of parts and operational conditions which have been herein described and illustrated in order to explain the nature of the invention may be made by those of ordinary skill in the art within the principles and scope of the invention.

Having thus set forth the nature of the invention, what is claimed is:

1. An apparatus for propelling a needle bearing device into biological tissue comprising:
an inner sleeve forming an open-ended longitudinal chamber therein for removably receiving said needle bearing device, said inner sleeve having first and second spaced apart recesses disposed in the outer surface thereof, said first recess being of a greater depth than said second recess;
an outer sleeve forming an open-ended longitudinal chamber therein for receiving and for permitting the movement therein of said inner sleeve between first and second positions, said outer sleeve having at least one aperture disposed therethrough;
biasing means for biasing said inner sleeve into said first position relative to said outer sleeve;
ball bearing means dimensioned to reside within said at least one aperture and to selectively reside within said second recess when aligned with said aperture when said inner sleeve is in said second position relative to said outer sleeve; and
locking sleeve means forming an open-ended longitudinal chamber therein for receiving and for permitting the movement therein between first and second positions of a portion of said outer sleeve adjacent to said at least one aperture disposed therein, said locking sleeve including an inner wall surface for forcing said ball bearing means into said second recess, when said outer sleeve is in said second position relative to said locking sleeve means, so as to lock the position of said inner sleeve relative to said outer sleeve, when said inner sleeve is in said second position thereof relative to said outer sleeve, longitudinal force on said locking sleeve means in a direction urging the same from said second position relative to said outer sleeve causing said ball bearing means to disengage said raised surface and said inner sleeve to shift position from said second position to said first position relative to said outer sleeve as a result of the action of said biasing means thereon, said first recess being provided to accept said ball bearing means during assembly of said apparatus, said first recess being of sufficient depth to permit the passage of said locking sleeve means over said ball bearing means during said assembly.

2. An apparatus in accordance with claim 1, wherein said first and second recesses are annular and are each disposed in planes substantially normal to the longitudinal axis of said inner sleeve.

3. An apparatus in accordance with claim 2, wherein said at least one aperture comprises a plurality of radially disposed apertures, said ball bearing means comprising a plurality of ball bearings, one of said ball bearings being disposed in each of said apertures.

4. An apparatus in accordance with claim 3, wherein said inner wall surface on the interior of said locking sleeve is annular, the edge of said inner wall surface being beveled to form a ramp to facilitate the movement of said ball bearings onto said inner wall surface.

5. An apparatus in accordance with claim 1, wherein said locking sleeve means comprises a collar portion and a nose portion, said nose portion having a tapered end for contact with said biological tissue.

6. An apparatus in accordance with claim 1, wherein said inner sleeve comprises clamp means for clamping a portion of said elongated device thereto to secure the same therein.

7. An apparatus in accordance with claim 1, wherein said biasing means comprises a helical spring.

8. An apparatus in accordance with claim 1, further in combination with a holder for a lancet or the like comprising an elongated body for disposition and retention within said inner sleeve, said elongated body further comprising retaining means for retaining a lancet or the like.

9. An apparatus in accordance with claim 8, wherein said retaining means comprises a depression disposed in one end of said elongated body, said depression dimensioned for frictionally retaining therein a portion of a lancet.

10. An apparatus in accordance with claim 8, wherein said holder further comprises a head, said shaft and head being simulative of a hypodermic syringe.

11. A lancet holder for use in conjunction with an apparatus for propelling the needle of a hypodermic syringe into biological tissue comprising:
an elongated body portion having first and second ends;
a head portion disposed at said first end of said elongated body portion, said head portion and said body portion substantially simulating the shape of a hypodermic syringe;
and retaining means for retaining a portion of a lancet disposed adjacent to said second end of said elongated body portion.

12. A lancet holder in accordance with claim 11, wherein said retaining means comprises a recess disposed in said second end of said elongated body, said recess dimensioned to capture and frictionally retain therein a portion of said lancet.

13. A lancet holder in accordance with claim 11, further comprising means for facilitating the grasping of said head portion by the user.

14. A lancet holder in accordance with claim 13, wherein said means for facilitating the grasping of said head portion comprises an annular recess disposed therein.

* * * * *